United States Patent
Kachaamy

(10) Patent No.: US 10,124,074 B2
(45) Date of Patent: Nov. 13, 2018

(54) INDIRECT CHROMOENDOSCOPY WITH AN ORAL INDIGO CARMINE BASE PREPARATION

(71) Applicant: Toufic Kachaamy, Phoenix, AZ (US)

(72) Inventor: Toufic Kachaamy, Phoenix, AZ (US)

( * ) Notice: Subject to any disclaimer, the term of this patent is extended or adjusted under 35 U.S.C. 154(b) by 860 days.

(21) Appl. No.: 14/471,040

(22) Filed: Aug. 28, 2014

(65) Prior Publication Data

US 2015/0238635 A1 Aug. 27, 2015

Related U.S. Application Data

(60) Provisional application No. 61/944,732, filed on Feb. 26, 2014.

(51) Int. Cl.
| | |
|---|---|
| *A61K 49/00* | (2006.01) |
| *A61K 47/10* | (2017.01) |
| *A61K 9/00* | (2006.01) |
| *A61B 1/04* | (2006.01) |

(52) U.S. Cl.
CPC ........ *A61K 49/006* (2013.01); *A61K 49/0071* (2013.01); *A61B 1/043* (2013.01)

(58) Field of Classification Search
None
See application file for complete search history.

(56) References Cited

U.S. PATENT DOCUMENTS

| 8,545,811 B2 | 10/2013 | Moro et al. |
|---|---|---|
| 2012/0251458 A1 | 10/2012 | De Sousa et al. |

FOREIGN PATENT DOCUMENTS

WO 2011110347 A2 9/2011

OTHER PUBLICATIONS

Canto, Staining in Gastrointestinal Endoscopy: The Basics; Endoscopy 1999; 31 (6): 479-486.*
Trivedi et al., Indications, stains and techniques in chromoendoscopy; Q J Med 2013; 106:117-131.*
Zippelius et al., Effects of Indigo Carmine on Human Chondrocytes in vitro; Open Orthop J. 2013; 7: 8-11.*
Mitooka et al., Chromoscopy of the colon using indigo carmine dye with electrolyte lavage solution, Gastrointestinal Endoscopy, vol. 38, No. 3, 1992.*
Hurlstone et al., "Detecting Diminutive Colorectal Lesions at Colonoscopy: A Randomised Controlled Trial of Pan-Colonic Versus Targeted Chromoscopy", GUT, 2004, vol. 53, No. 3, p. 376-380.
Lecomte et al., "Chromoendoscopic Colonoscopy for Detecting Preneoplastic Lesions in Hereditary Nonpolyposis Colorectal Cancer Syndrome",Clinical Gastroenterology and Hepatology, 2005, vol. 3, No. 9, p. 897-902

* cited by examiner

*Primary Examiner* — Michael G Hartley
*Assistant Examiner* — Nabila G Ebrahim
(74) *Attorney, Agent, or Firm* — Whitham & Cook, P.C.

(57) ABSTRACT

Indirect chromoendoscopy is performed by providing a subject with an orally administered composition which includes indigo carmine dye mixed with polyethylene glycol (PEG). Preferably, the subject ingests at least 160 mg of indigo carmine prior to the endoscopic procedure. This is accomplished by ingesting 1 ml to 6 L of a premixed or reconstituted indigo carmine and PEG composition up to twenty four hours prior to the endoscopic procedure.

3 Claims, 1 Drawing Sheet

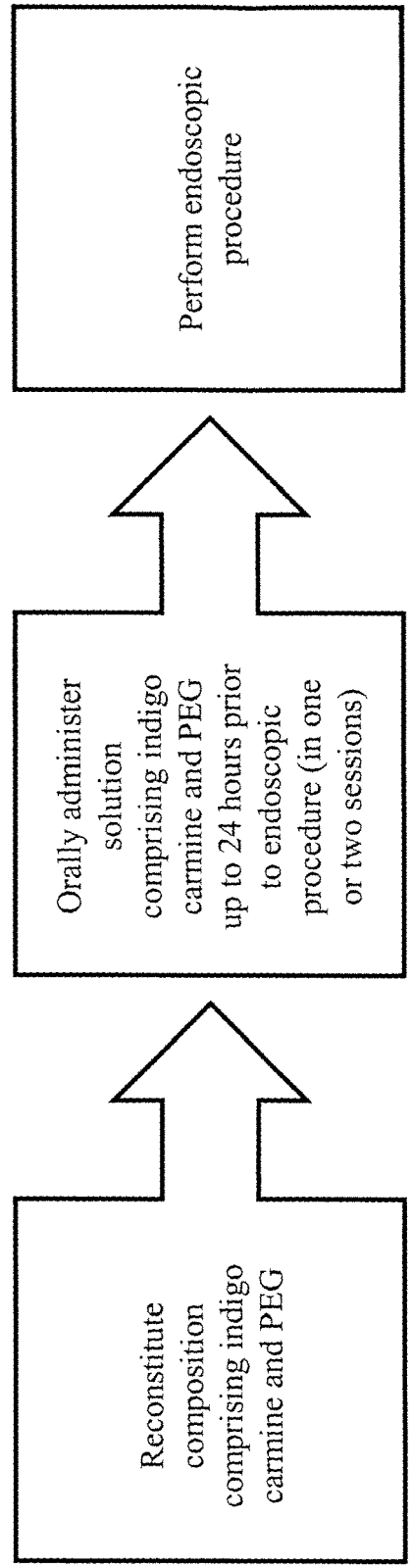

INDIRECT CHROMOENDOSCOPY WITH AN ORAL INDIGO CARMINE BASE PREPARATION

FIELD OF THE INVENTION

The invention relates to a pharmaceutical composition comprising indigo carmine mixed with polyethylene glycol and a method for staining the alimentary or gastrointestinal tract in preparation for a chromoendoscopic procedure.

BACKGROUND OF THE INVENTION

Colonoscopy is currently the preferred method for colon cancer screening. This procedure is used to examine the surface of the gastrointestinal tract for abnormalities, such as polyps consisting of abnormal growth into the lumen. When detected, these polyps can be removed thus decreasing the risk of colon cancer by an estimated 75 to 90% (Davila et al., 2006). However, the colonoscopy miss rate can be over 10% (Pickhardt et al., 2004). Cancers diagnosed after a colonoscopy, also called interval cancers, have multiple possible causes including a different biology than non-interval cancers and factors related to the procedure itself. Among procedural causes, missed lesions are thought to play a large role (Cooper et al., 2011; Pohl et al., 2010; Faiss S., 2011). There has been significant focus on flat lesions and specifically sessile serrated adenomas and their possible role in interval cancer. Flat polyps especially the sessile serrated adenomas are difficult to detect and may evolve more rapidly into cancer (Anderson J., 2011; Leggett et al., 2010).

For colonoscopy to continue to be the preferred method for colon cancer screening, its sensitivity must improve. Panchromoendoscopy using dyes including Indigo carmine or Methylene blue sprayed directly onto the surface of the colon has been shown to increase the sensitivity. However chromoendoscopy has not been widely adopted because it can be cumbersome and time-consuming (Coe et al., 2012). Chromoendoscopy remains the gold standard for polyp detection and should theoretically be performed routinely (Brown S. and Baraza W., 2010). However, time constraints continue to dictate that chromoendoscopy is employed only selectively.

Indirect chromoendoscopy offers the potential for more efficient use of chromoendoscopy. With indirect chromoendoscopy, the dye is administered orally thereby eliminating the time spent spraying the colon. Indirect chromoendoscopy has been attempted in the past with giving 100 mg of oral indigo carmine in the form of a capsule or powder before ingestion of the oral preparation (Mitooka et al., 1992). However, this method has not been adopted as it does not provide enough staining to improve polyp detection rate (Araujo et al., 2002). There is a need for new methods to enhance staining during chromoendoscopy in a more time-efficient and convenient manner.

SUMMARY OF THE INVENTION

Embodiments of the invention relate to a pharmaceutical composition comprising indigo carmine mixed with polyethylene PEG and a method for staining of the alimentary or gastrointestinal tract. The invention allows for more efficient performance of chromoendoscopy. Dye staining with this solution can significantly enhance lesion detection. The routine use of this technology will improve polyp detection rates and make its use a new standard of care.

Disclosed herein are pharmaceutically acceptable compositions of indigo carmine premixed with PEG. The composition may further comprise at least one of the following: sodium (Na), potassium (K), chloride (Cl), Bicarbonate ($HCO_3$), sulfate ($SO_4$) or simethicone. In some embodiments, the solution may also contain substances to prevent water absorption, improve palatability, decrease fluid shifts, decrease foaming, alter gastrointestinal motility, alter absorption, and improve tolerability. Preferably, the indigo carmine dye comprises at least 0.64 wt %.

In some embodiments, the solution comprising indigo carmine and PEG is orally administered in one session four to twenty-four hours before an endoscopic procedure. In other embodiments, the indigo carmine solution is orally administered in two sessions, the first session four to twenty-four hours before said endoscopic procedure and the second session one to four hours before said endoscopic procedure. Preferably, the dose provided to a subject is at least 160 mg of indigo carmine dye, and preferably 160-480 mg of indigo carmine dye. Preferably, the dose is provided with 1 ml to 6 liters of PEG.

DESCRIPTION OF THE FIGURE

FIG. 1 is a flow diagram illustrating an exemplary chromoendoscope procedure according to the present invention.

DETAILED DESCRIPTION OF THE INVENTION

Indigo carmine is FDA approved for use as a food colorant. Specifically, the FDA certifies up to 2 mg/kg of daily intake of indigo carmine, and there are no reports of toxicity from oral administration. If a 2 L solution of 0.008% of indigo carmine is ingested it would amount to a dose of 160 mg. Most of the oral solution will reach the colon intact. In rat studies, 3% of the dye taken orally was absorbed (Lethco et al., 1966). Data suggest that the food colorant absorbed in humans will be cleared very rapidly from circulation (Oravisto K., 1957). The combination of low levels of absorption, rapid clearance, and no known toxicity together make it unlikely that this food colorant would reach clinically significant concentrations, and thus indigo carmine dye will be well tolerated.

As further support of the safety of indigo carmine given for indirect chromoendoscopy, it is estimated that absorption through oral administration according to the methods of the present invention will lead to lower concentrations than what is currently used and accepted during intravenous administration. When used intravenously, indigo carmine is given in doses of 20 mg and 40 mg to diagnose ureteral injuries. Although there are rare case reports of hypotension, hypertension and anaphylaxis with the intravenous use of indigo carmine, causality has not been established (Jeffords et al., 1977; Shir et al., 1993; Gousse et al., 2000). If higher doses of oral indigo carmine are necessary to perform adequate panchromoendoscopy, they will be tolerated with minimal to no side effects.

Polyethylene Glycol (PEG) is a generic substance (sometimes referred to as polyethylene oxide or polyoxyethylene) used in multiple industries including colonic cleansing solutions. PEG is a well recognized excipient used in the pharmaceutical industry, and is also a well recognized constituent in a number of laxatives (e.g., MiraLAX and Dulcolax) PEG is available in substituted and unsubstitute forms. Indigo carmine has been used to stain colonic polyps for better identification, and studies have shown that if sprayed topically during an endoscopic procedure, it improved detection of abnormalities. Combining both materials and having the patient ingest them will pre-stain the colon for colonoscopy and save time, as spraying is not usually done because it is cumbersome and time consuming and does not lead to uniform staining. The present invention will help endoscopists perform chromoendoscopy more efficiently, without the need to spend time spraying the dye, and help to improve detection of polyps. Endoscopists can be provided with educational material and videos of examples of how to use the composition.

Embodiments of the invention thus provide methods of staining the alimentary or gastrointestinal (GI) tract of a subject. The methods comprise orally administering to a subject a composition comprising PEG mixed with indigo carmine dye. The premixed composition, which provides higher than normal doses of indigo carmine, produces significantly better staining of the alimentary and gastrointestinal tract as compared to more traditional methods. This premixed composition thus allows for increased visualization of colonic lesions.

Embodiments of the invention provide premixed compositions which are in liquid or reconstitutable form (e.g., assume a liquid format on the addition of water or aqueous fluid) comprising indigo carmine dye mixed with PEG. The compositions are orally ingestible and may contain one or more other ingredients, e.g. salts and ionized forms thereof, (e.g. $Na^+$, $K^+$, $Cl^-$, $HCO_3^-$, $SO_4^{2-}$, etc). The composition may also contain other beneficial substances such as flavorings, colorants, buffering agents, thickeners, wetting agents, etc. In exemplary embodiments, the composition is formulated to provide indigo carmine at doses ranging from 160 mg to 10 g (and in certain embodiments, 150-500 mg or 160 mg to 480 mg and other comparable ranges). The indigo carmine dye is mixed with PEG and one or more of sodium, potassium, chloride, bicarbonate, $SO_4$, and the anti-foaming agent simethicone, and preferably has an osmolality between 270 and 290. The constituents have concentrations within the following ranges:

| | |
|---|---|
| $Na^+$ (mEq/L) | 0 to 150 |
| $K^+$ (mEq/L) | 0 to 100 |
| $Cl^-$ (mEq/L) | 0 to 100 |
| $HCO_3^-$ (mEq/L) | 0 to 100 |
| $SO_4^{2-}$ (mEq/L) | 0 to 100 |
| PEG (gm/L) | 0 to 200 |
| Simethicone (gm/L) | 0 to 1500 |

The molecular weight of the PEG can vary from low molecular weights (e.g., 300-400 MW) to high molecular weights (5000 MW and above), and the liquid composition used in the invention could include a mixture of PEG at different molecular weights.

The indigo carmine and PEG composition can be provided in a container to be mixed before use with water. The indigo carmine and PEG composition can, for example, be administered in one or two sessions based on the patient's and/or healthcare provider's preference and indication. In a non-split preparation protocol, up to 6 liters of the solution may be consumed in one session four to twenty-four hours before the endoscopic procedure. In a split preparation protocol, a portion of the preparation with or without indigo carmine may be consumed four to twenty-four hours before the procedure and a second portion may be consumed one to four hours before the procedure. Each portion of the split preparation can range from 1 ml to 6 liters (and in some embodiments 100 ml to 4 liters or 250 ml to 2 liters, and other comparable ranges).

Capsule chromoendoscopy has been attempted in the past with mixed results. Mitooka and colleagues attempted oral administration of 100 mg of indigo carmine powder before the colonic prep and found it to give a good effect in 80% of the cases on the right colon and 50% of the left colon. No side effects were observed (Mitooka et al., 1992). Araujo and colleagues administered 100 mg of oral indigo carmine in a capsule before the colonic prep and found that it was ineffective in staining the entire colon in over 90% of the cases (Araujo et al., 2002).

Embodiments of the present invention provide methods to enhance the staining when compared to capsule chromoendoscopy. Unlike capsule chromoendoscopy, the indigo carmine dye is premixed with PEG. The premixed indigo carmine and PEG composition can also be reconstituted from a powdered or dried form. Providing a mixed solution assures distribution of the indigo carmine dye in the gastrointestinal tract. Also, having higher doses of indigo carmine than previously used, allows for better staining results. The mixture can be administered starting twenty-four hours before the endoscopic procedure (e.g. colonoscopy). Volumes of the solution orally administered can range from 1-5 ml to 6 liters (and in some embodiments 100 ml to 4 liters or 250 ml to 2 liters, and other comparable ranges).

Embodiments of the invention also provide methods of performing endoscopic procedures which require or for which it is beneficial to stain tissue or cells that are to be examined. The methods include administering to a subject (e.g. orally or by rinsing or washing) a composition comprising PEG and indigo carmine dye, and then carrying out the endoscopic procedure. The endoscopic procedures include but are not limited to: investigation of any portion of the GI tract, including the esophagus, stomach and duodenum (esophagogastroduodenoscopy); small intestine (enteroscopy); large intestine/colon (colonoscopy, sigmoidoscopy); bile ducts, rectum (rectoscopy) and anus (anoscopy) (both also referred to as "proctoscopy"). However, other applications of the technology are also possible in which tissues or cells are exposed to the composition (e.g. via washing or rinsing with a PEG-indigo carmine composition) and stained thereby. In such embodiments, the composition is not necessarily ingestible or "food grade" but is physiological compatible. Cells that may be stained and examined include tissues or cells of the respiratory tract, the nose (rhinoscopy), the lower respiratory tract (bronchoscopy), the ear (otoscopy), the urinary tract (cystoscopy), the female reproductive system (gynoscopy), the cervix and/or vagina (colposcopy), the uterus (hysteroscopy), the fallopian tubes (falloposcopy), and normally closed body cavities (e.g. accessed through a small incision) such as the abdominal or pelvic cavity (laparoscopy), the interior of a joint (arthroscopy), organs of the chest (thoracoscopy and mediastinoscopy), etc.

Embodiments of the invention also include methods of identifying abnormal cells by exposing cells, tissue, organs, etc. suspected of containing abnormal cells or growths (e.g. cancerous or precancerous cells, polyps, tumors, etc.). The methods include exposing cells, tissue, organs, etc. that may contain such abnormalities to the composition of the invention, viewing and/or imaging the stained cells, tissue, organs, etc., and concluding whether or not the stained cells are normal or abnormal. The methods may include steps of comparing the viewed or imaged cells to reference cells (e.g. normal cells and/or known abnormal or diseased cells), in order to recognize similarities and differences, then concluding whether or not the stained cells are normal or abnormal based on the comparison.

While invention has been described in its preferred embodiments, those of skill in the art will recognize the invention can be practiced with variations within the spirit and scope of the appended claims.

REFERENCES

Throughout this application, various references describe the state of the art to which this invention pertains. The disclosures of these references are hereby incorporated by reference into the present disclosure.

Anderson J C. (2011) Risk factors and diagnosis of flat adenomas of the colon. Expert Rev Gastroenterol Hepatol. February; 5(1):25-32.

Araujo S. et al. (2002) Efficacy of contrast chromoendoscopy of the colon with the use of indigo carmine administered orally. Arq Gastroenterol. vol. 39 no. 3 September Brown S R et al. (2010) Chromoscopy versus conventional endoscopy for the detection of polyps in the colon and rectum. The Cochrane Library, Issue 10

Coe S G, Wallace M B. (2012) Colonoscopy: new approaches to better outcomes. Curr Opin Gastroenterol. January; 28(1):70-5.

Cooper G S, Xu F, Barnholtz Sloan J S, Schluchter. (2011) Prevalence and predictors of interval colorectal cancers in Medicare beneficiaries. Cancer. October 11. doi: 10.1002/cncr. 26602

Davila, R., Rajan, E., Baron, T., (2006) ASGE guideline: colorectal cancer screening and surveillance. GASTROINTESTINAL ENDOSCOPY Volume 63, No. 6: 2006

Faiss S. (2011) The missed colorectal cancer problem. Dig Dis. 29 Suppl 1:60-3. Epub November 15.

Gousse A E, Safir M H, Madjar S, Ziadlourad F, Raz S. (2000) Life-threatening anaphylactoid reaction associated with indigo carmine intravenous injection. Urology. September 1; 56(3):508

Jeffords D L, Lange P H, DeWolf W C. (1977) Severe hypertensive reaction to indigo carmine. Urology; 9:180-1.

Leggett B, Whitehall V. (2010) Role of the serrated pathway in colorectal cancer pathogenesis. Gastroenterology. June; 138(6):2088-100.

Lethco E J, Webb J M J. (1966) The fate of F D&C blue no. 2 in rats. Pharmacol Exp Ther. November; 154(2):384-9

Mitooka H, Fujimori T, Ohno S, Morimoto S, Nakashima T, Ohmoto A, Okano H, Miyamoto M, Oh T, Saeki S. (1992) Chromoscopy of the colon using indigo carmine dye with electrolyte lavage solution. Gastrointest Endosc. May-June; 38 (3):373-4

Oravisto K J. (1957) Investigations into the excretion mechanism of indigo carmine in normal human kidney. Ann Chir Gynaecol Fenn Suppl. 46(2):1-79

Pickhardt P., Nugent, P., Mysliwiec, P., et al. (2004) Location of adenomas missed by optical colonoscopy. Ann Intern Med 2004; 141:352

Pohl H, Robertson D J. (2010) Colorectal cancers detected after colonoscopy frequently result from missed lesions. Clin Gastroenterol Hepatol. October; 8(10):858-64. 22.

Shir Y, Raja S N. (1993) Indigo carmine—induced severe hypotension in patients undergoing radical prostatectomy. Anesthesiology 79.

The invention claimed is:

1. A pharmaceutical composition suitable for oral administration for use in staining of the alimentary or gastrointestinal tract consisting of indigo carmine dye mixed with polyethylene glycol (PEG) that provides an administered dose of at least 160 mg of said indigo carmine dye in the form of a reconstitutable powder or premixed solution.

2. A pharmaceutical composition suitable for oral administration consisting of indigo carmine dye mixed with PEG in liquid or reconstitutable form wherein said indigo carmine dye comprises at least 0.64 wt %.

3. The composition of claim 1 wherein said dose of indigo carmine dye ranges from 160 mg to 10 g in 1 ml to 6 liters of PEG.

* * * * *